US011591635B2

(12) United States Patent
Inui et al.

(10) Patent No.: US 11,591,635 B2
(45) Date of Patent: Feb. 28, 2023

(54) SCREENING METHOD

(71) Applicant: MARS, INCORPORATED, McLean, VA (US)

(72) Inventors: Taichi Inui, Leicestershire (GB); Richard Mark Haydock, Leicestershire (GB)

(73) Assignee: Mars, Incorporated, McLean, VA (US)

( * ) Notice: Subject to any disclaimer, the term of this patent is extended or adjusted under 35 U.S.C. 154(b) by 99 days.

(21) Appl. No.: 16/962,474

(22) PCT Filed: Jan. 15, 2019

(86) PCT No.: PCT/US2019/013694
§ 371 (c)(1),
(2) Date: Jul. 15, 2020

(87) PCT Pub. No.: WO2019/140455
PCT Pub. Date: Jul. 18, 2019

(65) Prior Publication Data
US 2021/0079446 A1 Mar. 18, 2021

(30) Foreign Application Priority Data

Jan. 15, 2018 (GB) .................................. 1800632
Mar. 21, 2018 (GB) .................................. 1804489

(51) Int. Cl.
*C12Q 1/527* (2006.01)
*C12Q 1/02* (2006.01)
*C12Q 1/18* (2006.01)
*G01N 21/64* (2006.01)

(52) U.S. Cl.
CPC ............ *C12Q 1/527* (2013.01); *C12Q 1/025* (2013.01); *C12Q 1/18* (2013.01); *G01N 21/64* (2013.01); *G01N 2469/00* (2013.01); *G01N 2496/00* (2013.01)

(58) Field of Classification Search
None
See application file for complete search history.

(56) References Cited

U.S. PATENT DOCUMENTS

| 8,012,514 B2 | 9/2011 | Maxwell |
| 2012/0244098 A1 | 9/2012 | Starkenmann et al. |

FOREIGN PATENT DOCUMENTS

EP 2172767 A1 4/2010

OTHER PUBLICATIONS

Nakano, Manabu, et al. "Inactivating effects of the lactoperoxidase system on bacterial lyases involved in oral malodour production." Journal of medical microbiology 64.10 (2015): 1244-1252. (Year: 2015).*

Suehiro Y, Sakai K, Nishioka M, Hashimoto S, Takami T, Higaki S, Shindo Y, Hazama S, Oka M, Nagano H, et al. Highly sensitive stool DNA testing of Fusobacterium nucleatum as a marker for detection of colorectal tumours in a Japanese population. Ann Clin Biochem. 2017;54:86-91. (Year: 2017).*

Natsch, Andreas, Joachim Schmid, and Felix Flachsmann. "Identification of Odoriferous Sulfanylalkanols in Human Axilla Secretions and Their Formation through Cleavage of Cysteine Precursors by a C? S Lyase Isolated from Axilla bacteria." Chemistry & biodiversity 1.7 (2004): 1058-1072. (Year: 2004).*

Troccaz, Myriam, et al. "Properties of recombinant *Staphylococcus haemolyticus* cystathionine ß-lyase (metC) and its potential role in the generation of volatile thiols in axillary malodor." Chemistry & biodiversity 5.11 (2008): 2372-2385. (Year: 2008).*

Salako et al. "Comparison of the use of the Halimeterand the Oral Chroma™ in the assessment of the ability of common cultivable oral anaerobic bacteria to produce malodorous volatile sulfur compounds from cysteine and methionine." Medical Principles and Practice 20.1 (2011): 75-79. (Year: 2011).*

Coil, David A., et al. "Draft genome sequences of 26 Porphyromonas strains isolated from the canine oral microbiome." Genome announcements 3.2 (2015): e00187-15. (Year: 2015).*

Dewhirst, Floyd E., et al. "The canine oral microbiome." PloS one 7.4 (2012): e36067. (Year: 2012).*

Akihiro Yoshida, et al, Hydrogen sulfide production from cysteine and homocysteine by periodontal and oral bacteria, Journal of Periodontology, Nov. 2009, pp. 1845-1851, vol. 80, No. 11.

Allaker, Investigations into the micro-ecology of oral malodour in man and companion animals, J. Breath Res, Mar. 2010, p. 17103, vol. 4, No. 1.

T. Clausen, et al, Slow-Binding Inhibition of *Escherichia coli* Cystathionine Beta-Lyase by L-Aminoethoxyvinylglycine: A Kinetic and X-ray Study, Biochemistry, Oct. 14, 1997, pp. 12633-12643, vol. 36, No. 41.

Dadamio, et al, A novel and visual test for oral malodour: first observations, J. Breath Res., Aug. 2011, p. 046003, vol. 5, No. 4.

Gerusa N.A. Senhorinho, et al, Occurrence and antimicrobial susceptibility of *Porphyromonas* spp. and *Fusobacterium* spp. in dogs with and without periodontitis, Anaerobe, Mar. 2012, pp. 381-385, vol. 18, No. 4.

Greenberg, et al, Compressed Mints and Chewing Gum Containing Magnolia Bark Extract Are Effective Against Bacteria Responsible for Oral Malodor, J. Agric. Food Chem., Oct. 2007, pp. 9465-9469, 55, 23.

Holcombe, et al, Early Canine Plaque Bio, Characterization of Key Bacterial Interactions Involved in Initial Colonization of Enamel, PLoS ONE, Dec. 2, 2014, p. e113744. https://doi.org/10.1371/journal.pone.0113744, 9 (12).

(Continued)

*Primary Examiner* — Robert J Yamasaki
(74) *Attorney, Agent, or Firm* — Bookoff McAndrews, PLLC

(57) ABSTRACT

A method for screening substances for their ability to reduce malodours from emanations from an animal, said method comprising determining the effect of said substances on the C-S lyase activity of bacteria that emit volatile sulphuric compounds (VSCs), by contacting a test substance with a sample comprising said bacteria or a supernatant obtainable from a culture of said bacteria in the presence of a substrate for a C-S lyase, detecting the levels of thiol production from said bacteria, and comparing the results with those obtained from similar bacteria in the absence of said substance.

18 Claims, 13 Drawing Sheets

(56) References Cited

OTHER PUBLICATIONS

Jarosz, A.P., et al, Microplate-Based Colorimetric Detection of Free Hydrogen Sulfide, Analytical Chemistry, Mar. 11, 2013, pp. 3638-3643, vol. 85.

Jeusette, et al, 24-hour evaluation of dental plaque bacteria and halitosis after consumption of a single placebo or dental treat by dogs, American J. Vet. Res, Sep. 2016, pp. 613-619, vol. 77, issue No. 6.

K Vidya Hiranmayi, et al, Novel Pathogens in Periodontal Microbiology, J. Pharm. Bioallied Sci., Jul.-Sep. 2017, 9 (3); 155-163.

M. Egert, et al, Identification of compounds inhibiting the C-S lyase activity of a cell extract from a *Staphylococcus* sp. isolated from human skin, Letters in Applied Microbiology, Sep. 23, 2013, pp. 534-539. Available online: https://onlinelibrary.wiley.com/doi/abs/10.1111/lam.12146., vol. 57, No. 6.

Milella, The Negative Effects of Volatile Sulphur Compounds, J Vet Dent, Summer 2015, 32(2):99-102.

Montoya, L.A., et al, Development of Selective Colorimetric Probes for Hydrogen Sulfide Based on Nucleophilic Aromatic Substitution, The Journal of Organic Chemistry, Jun. 4, 2013, pp. 6550-6557, vol. 78.

N/A, Hydrogenated Vegetable Oil, Hydrogenated Vegetable Oil, Jan. 31, 2019, pp. 1-9, n/a, Wikepedia.

Neil Culham, et al, Oral Malodor and its Relevance to Periodontal Disease in the Dog, Journal of Veterinary Dentistry, Dec. 24, 1998, pp. 165-168, vol. 15, No. 4.

Yu, Shin-Hye, et al, Decrease of insoluble glucan formation in *Streptococcus* mutans by co-cultivation with Enterococcus faecium T7 and glucanase addition, Biotechnology Letters, Nov. 21, 2017, pp. 375-381, vol. 40, No. 2.

Zhang, et al, Colorimetric detection of biological hydrogen sulfide using fluorosurfactant functionalized gold nanorods, Analyst, Sep. 2015, pp. 7443-7450, 140.

\* cited by examiner

SCREENING METHOD

CROSS REFERENCE TO RELATED APPLICATIONS

This application is a national stage application, filed under 35 U.S.C. § 371, of International Application No. PCT/US2019/013694, filed on Jan. 15, 2019, which claims priority to UK Patent Application Number GB 1800632.0, filed on Jan. 15, 2018 and UK Patent Application Number GB 1804489.1, filed on Mar. 21, 2018, for which the entire contents of each are hereby incorporated by reference in their entirety.

FIELD

The present invention relates to a method for screening for substances of compositions that can reduce malodour in the emanations, including the breath or faeces, of an animal, in particular a companion or pet animal such as a pet animal like a dog or cat.

BACKGROUND

In order to ensure good animal welfare in particular amongst domestic pets, it is important to ensure that a positive connection exists between pet and owner. The occurrence of unpleasant odours emanating from the animal, in particular in the form of bad breath or halitosis, but also in connection with highly malodourous faecal matter, can be detrimental to such relationships. In fact, canine oral malodour is considered to be a barrier for pet ownership.

There are a number of products on the market which aim to improve animal oral health. These are primarily designed to be efficacious against plaque or tartar on the tooth surface, or along the gum line. These may, as a consequence, have some impact on bad breath of the animal. However, it would be desirable to have or to develop products which specifically target malodour, in particular oral malodour. Indeed, there is evidence that the compounds responsible for oral malodour can be toxic to tissues and contribute to the pathogenesis of periodontal disease (Milella, 2015 J Vet Dent. 32(2): 99-102). Desirably, such products would be designed to target the root cause of the malodours and not merely provide a masking effect.

Since sensitivity to malodours will be variable from one individual to another, in order to develop such products, it is necessary to provide a scientific basis for determining efficacy which is not subjective in nature, and which is amenable to use in high-throughput screening.

Bacteria found in the oral cavity or in faecal matter of companion animals such as dogs and cats, is known to be different to that found in humans and it has been recognised that cognisance has to be taken of this when developing products to counter periodontal disease of such animals (see Holcombe et al. PLoS ONE, 2014, 9(12) p. e113744).

The leading cause of bad breath or halitosis in humans has been reported as being volatile sulphur compounds (VSCs), produced by oral bacteria, and in particular gram negative bacteria, which thrive predominantly at the dorsum of the tongue. Attempts to counter this have focused on the use of antimicrobial compounds or substances which target these particular bacteria (Greenberg et al., J. Agric. Food Chem. 2007, 55, 9465-9469).

It has been reported that it is also VSCs which give drive the perception of oral malodour in companion animals (Culham 1998 J Vet Dent 15(4): 165-168). Such VSCs may include the products of sulfuric amino acid breakdown, including hydrogen sulphide and the sulphydryl anion as well as methyl mercaptan.

There have been no reported studies to identify the specific types of bacteria that give rise to malodour in the oral cavity of companion animals. Since the bacterial population found in such animals is different to that found in humans, there is no reason to believe that the VSC producing bacteria will be the same as those found in humans. As a result, compounds which may be effective to combat malodour in humans may not be effective for administration to animals.

It is important therefore to develop methods for identifying compounds that may be used to address this problem in an efficient and effective manner.

A screening method for the identification of compounds that inhibit the C-S lyase activity of specifically *Staphylococcus* species, isolated from human skin has been reported previously (Egert et al., Letter in Applied Microbiology, (2013), 57, 534-539). In that case, a homogenate produced by lysing the bacteria under highly stringent conditions was tested for its ability to produce VSCs. However, this method was specific for a particular bacterial species not found in the mouth of a companion animal. Furthermore, the method was not used in a high throughput screen. For such screens, a consistent and readily available starting material is a prerequisite and therefore the use of a homogenate, which needs to be produced in a batch process, and may be variable from batch to batch, would not be desirable. Compounds tested were intended for cosmetic use, and therefore may not be acceptable for oral administration.

SUMMARY

Accordingly, there is provided a method for screening substances for their ability to reduce malodours from emanations from an animal, in particular a companion animal. The method comprises determining the effect of said substances on the C-S lyase activity of bacteria that emit volatile sulphuric compounds (VSCs) by contacting a test substance with a sample comprising said bacteria or a supernatant obtainable from a culture of said bacteria, in the presence of a substrate for a C-S lyase, detecting the levels of thiol production from said bacteria, and comparing the results with those obtained from similar bacteria in the absence of said substance.

The method of the invention provides an efficient and effective in vitro screening method, with a good expectation that substances which impact on bacterial C-S lyase activity will have an impact on VSC emission and thus reduce malodour from the said companion animal. If a substance is able to inhibit the enzyme activity, for example by inhibiting or killing the bacteria, it would be expected to be of use in the context of the product that may be administered to a companion animal to reduce, minimize or eliminate malodours.

The applicants have found that there is no need to produce a homogenate of the bacteria to release the C-S lyase enzyme prior to detection of thiol production. This suggests that the enzyme is present in the medium and so is either secreted by the bacteria, or is in the residue from dead bacteria. As a result, a supernatant, obtained by simply removing cells from a VSC producing bacterial culture, for example by filtration, may also be employed.

There is no requirement for a preliminary homogenisation step or bacterial lysis step, and so this provides a significant advance over the method of Egert et al. supra. As a result, the procedure is simpler and more amenable to being used in a high throughput screening process, since it can be carried out using a 'stock' bacterial culture or a simple supernatant, including a cell-free supernatant, obtainable directly from a bacterial culture.

Thus, the method of the invention does not include homogenisation and/or lysis steps. Rather, in the method if the invention a test substance is contacted with a sample comprising the bacteria itself (i.e. intact, whole bacterial cells) or a supernatant obtainable from a culture of the bacteria.

As used herein, the expression 'high throughput screening process' refers to processes which can test multiple compounds for example 50 or more compounds for example from a compound library, simultaneously, using a procedure which is at least partially automated.

When the sample comprises live bacteria, it more closely mimics the situation found within the oral cavity in particular, since in those cases, it is live bacteria that effect or contribute to the amino acid breakdown. As a result, the screening method of the invention more closely resembles that found in the 'live' situation and so compounds positively identified may be more likely to be effective in those situations.

A particular example a C-S lyase whose activity can be determined using the method of the invention includes cystathione-β-lyase. C-S lyase enzymes cleave amino acids to produce thiols and VSCs. Thus, suitable substrates for the enzymes for use in the method include sulphur containing amino acids, in particular cysteine, methionine, or derivatives of these such as benzylcysteine.

The levels of thiol production from the bacteria are suitably detected using a method which is amenable to high-throughput screening. Such methods may include Gas Chromatography (GC) techniques, although these may require complex laboratory equipment.

In some instances, thiol production is detected using a fluorometric method, where a fluorescent signal is generated by the presence of thiol and this signal may be assessed either qualitatively or quantitatively using a fluorimeter. A fluorimeter may be used to efficiently and effectively determine the signal of multiple samples simultaneously, for example, where these are arranged in wells of a multi-well plate such as a 96-well plate or even a 384-well plate.

The levels of activity of the enzyme may be determined fluorometrically, by culturing the bacteria in the presence of both the substrate for the enzyme, such as benzylcysteine, and fluorescent signalling reagent such as a bimane dye derivative, for instance, a halobimane such as monobromobimane (3-(bromomethyl)-2,5,6-trimethyl-1H,7H-pyrazolo[1,2-a]pyrazole-1,7-dione). In the presence of thiols generated by the C-S lyase activity, the halo group becomes displaced by the thiol, resulting in the thiol acquiring a fluorescent label, which can be detected following illumination in a fluorimeter, at the appropriate wavelength. Any reduction in fluorescent signal between a sample of bacteria cultured in the presence of a test substance as compared to the signal generated by a similar sample but in the absence of such test substance will be indicative of a beneficial effect.

Where live bacteria are used in the method, they may be contacted with the test substances in culture. Thus conventional incubation methods and media may be utilised. Aerobic or anaerobic conditions may be used depending upon the particular bacteria being cultured, but in a particular embodiment, the bacteria are cultured anaerobically.

Bacterial samples used in the method are suitably cultured at physiologically acceptable temperatures for example in the range of 20-60° C., such as from 25-40° C., and in particular at 37° C. A suitable culture medium, such as Brain Heart Infusion (BHI) media is suitably employed to support the bacteria during the culture process.

Samples are suitably incubated with the test substance for sufficient time to allow a clear and detectable signal to develop. This will depend upon factors such as the precise detection method used and the concentration of bacteria present in the sample, but will typically be in the range of from 5 minutes to 180 minutes, such as from 20-120 minutes, for example from 40-75 minutes (1 hour 15 minutes).

The sample size used in the method may be quite small, in particular where the fluorometric method described above is employed. Sample sizes may suitably be in the range of from 1-1000 μL, for example from 10-300 μl, or from 25-250 μl. The use of small samples is particularly efficient for high throughput screening purposes.

Where an enzymatic activity level is measured, the concentration of bacteria may be quite low. For example, the culture may be one having an optical density measured at a wavelength of 600 nm (OD600) in the range of from 0.05 to 1.0, for example about 0.5.

An excess of the enzyme substrate such as benzylcysteine may be included in the sample under test, to ensure that a clear signal is obtained, which is indicative of the level of enzyme present. The precise amount of substrate used will depend upon factors such as the amount and type of bacteria present, but will typically be in the range of from 1-10 mM, for example about 4 mM.

The concentration of the signalling moiety such as the fluorescent dye (for instance, the bimane dye) will also vary depending upon the nature of the dye, the concentration of the bacteria and the nature and amount of enzyme substrate added. However, typically the dye such as monobromobimane is present at a concentration of from 10-500 mM, for example about 100 mM.

A co-enzyme such as pyridoxal-5'-phosphate may also be added to the sample to catalyse the enzymatic reaction. The concentration of the co-enzyme will vary depending upon the nature of the co-enzyme and the enzyme, as well as the concentration of the bacteria, but will typically be in the range of from 0.1-200 μM, for example about 10 μM.

The amount of test substance used in the method should be at a concentration that would be orally acceptable as described below, if administered to a companion animal. This will vary depending upon the nature of the substance. Typically however, the substance will be added in a concentration of from 1 to 500 μM.

The bacteria used in the method may be of any bacterial strain that emits VSCs. Desirably, the bacterial strain is able to emit high levels of VSCs under normal conditions, as this will provide a greater degree of sensitivity in the test. Such strains may include for example, certain *Escherichia coli* strains, including the type strain DH5.

Levels of VSCs emitted may be determined using any of the techniques described above. What constitutes 'high levels' of VSC emission in accordance with the present invention are levels which are at least equivalent to those emitted from *Fusobacterium nucleatum*. This can be measured using any of the test methods described herein, including the lead acetate method, where the results obtained from the test strain would be at least as dark, or darker than those obtained using *F. nucleatum*.

In some embodiments, the bacteria used in the test is a sample of a strain which is found either in the oral cavity of said animal or in faecal matter from said animal. In this instance, screening methods can be provided which are specific for the particular animal. Desirably, the animal is a companion animal such as a dog or cat, but the method may also be used for humans.

Thus, the bacteria used in the method may be one or more bacteria which has been identified as being present in the oral cavity or in faecal matter of a particular type of companion animal, such as a dog or cat. This may be determined using conventional methods, for example by analysis of bacterial strains found in faecal matter, of from the oral cavity, in particular, in plaque biofilms such as subgingival plaque, or from saliva, the buccal region or dorsum part of the tongue, of one or more companion animals.

Once a population of such bacteria has been identified, those which are emitters of VSCs and in particular, high emitters of VSCs may be identified, and selected as the one or more bacteria for use in the screening method. Identification of the key bacteria is suitably done by empirical means using techniques known in the art, for example fluorometric methods described above.

However, other methods may also be employed at this stage. For example, the emission of VSCs and in particular hydrogen sulfide may be determine colourimetrically, by using a reagent such as lead acetate or bismuth trichloride, which changes colour and in particular, forms a black coloration or precipitate when mixed with hydrogen sulfide. Other colorimetric techniques include the use of functionalised gold nanorods as described for example by Zhang et al. Analyst, 140(21):7443-7450, the content of which is incorporated herein by reference. VSC emitters may also be detected using methods such as the detection of amines in saliva using a mixture of cadervrine and putrescine, (Dadamio et al. Journal of Breath Research, 5(4); 2011, 046003, the content of which is incorporated herein by reference) as this positively correlates with VSC production. UV absorption methods may be used to monitor VSC production, for example using a microplate coated with Nafion polymer doped with silver ions, which react with volatile hydrogen sulfide to produce $Ag_2S$ nanoparticles which have strong absorbance in the low UV range (Jarosz et al. (2013) Chemistry, 85(7): 3638-3643, the content of which is incorporated herein by reference) or the production of nitrobenzofurazan (Montoya et al. (2013) J. Org. Chem. 78(13): 6550-6557, the content of which is incorporated herein by reference).

For example, the bacteria may be cultured in a closed vessel which contains a strip of lead acetate paper. When exposed to hydrogen sulphide, the lead acetate is converted to lead sulphide which is black, and thus the paper darkens. This colour change may be assessed either visually, or using a spectrometer, and the result compared with strips obtained from other bacteria under similar conditions. The darker the resultant paper, the higher the level of VSC emitted by that particular bacteria.

Alternatively, bismuth trichloride may be added to a culture so that the appearance of a black precipitate is indicative of the presence of hydrogen sulfide.

Such methods however, may require significant human intervention. Furthermore, the applicants have found that their detection limits are above the human olfaction threshold, and so they may not be particularly useful in the present screening method where the aim would be to reduce the VSC level to well below the detection limit of the test. However, such methods may be useful for the identification of the highest VSC emitters from amongst a population of bacteria found in the oral cavity or faecal matter of a companion animal.

Thus in some embodiments, the method further comprises a step of determining the level at which bacteria found in the oral cavity or faecal matter emit VSCs and selecting bacteria for use in the method which emit the higher levels of VSCs.

However, other factors may also be taken into account in the selection of bacteria for use in the test, including the ability or association of a particular bacteria with disease such as gingivitis and periodontitis. In such cases, it would be useful to use such bacteria in the method of the invention as any compounds may then be associated with a dual activity, in so far as they may also treat or prevent disease, as well as reduce malodour.

Desirably, the bacteria used in the method are found in the oral cavity or faecal matter of a dog, in particular bacteria found in the oral cavity of a dog.

Bacterial strains obtainable from the oral cavity of a companion animal and in particular dogs, may include *Bacteroides* species, *Bacterioides heparinolyticum*, *Bergeyella* species such as *Bergeyella zoohelcum*, *Campylobacter* species, *Capnocytophaga* species, *Chloroflexi* species, *Fusobacterium* species such as *Fusobacterium nucleatum* (which may occur in the oral cavity of humans as well as companion animals), *Lachnospiraceae* species, *Moraxella* species, *Neisseria* species such as *Neisseria animaloris* or *Neisseria zoodegmatis*, *Pasteurella* species such as *Pasteurella dogmatis*, *Peptostreptococcaceae* species such as *Peptostreptococcus hiranonis*, *Porphyromonas* species such as *Porphyromonas cangingivalis*, *Porphyromonas gingivicanis*, *Porphyromonas gulae* or *Porphyromonas macacae*, or *Synergistales* species.

In a particular embodiment, the bacteria used are other than a *Staphylococcus* species.

In a particular embodiment, the bacteria used in the method are one or more bacteria selected from the group listed in Table 1 below and in particular are selected from the group consisting of *Escherichia coli* DH5α, *Porphyromonas macacae* (in particular *Porphyromonas macacae* COT-192 OH2631 (Genbank Accession no. NZ_JRFB00000000), *Synergistales* sp., *Peptostreptococcus hiranonis*, *Fusobacterium nucleatum* and *Neisseria zoodegmatis*.

In a particular embodiment, the bacteria used in the method are one or more bacteria selected from the group consisting of *Escherichia coli* DH5α, *Porphyromonas macacae* COT-192 OH2631 (Genbank Accession no. NZ_JRFB00000000) or *Synergistales* sp.

The selection of specific bacteria as described above for use in a method for screening substances for their ability to reduce malodours from emanations from a companion animal and in particular a dog may form a further aspect of the invention. Thus for example, there may be provided a method for screening a test compound for its ability to reduce malodours from emanations from a companion animal, said method comprising determining the effect of said compound on the emission of volatile sulphuric compounds (VSCs) from one or more bacteria found either in the oral cavity of said animal or in faecal matter from said animal, wherein the bacteria is selected from the strains defined hereinbefore. In such cases, the method used for the determining the effect of the compound on the emission of VSCs may vary, and may include any of the methods suggested herein.

Suitably the method will be carried out using more than one strain of bacteria, and in particular up to 5 different strains of VSC emitting bacteria. Bacteria may be oral bacteria or fecal bacteria or in a particular embodiment, a combination of both. Bacteria of different strains may be tested individually or in combined cultures where available. Desirably however, the or each bacterial culture used in the method comprises a single strain, as this provides better reliability and consistency across the screening process.

Where used, faecal bacteria may be isolated from faecal matter using conventional isolation techniques, for example as illustrated in the Example hereinafter.

The substances selected from the screening method are desirably those which inhibit VSC production from more than one and preferably all of the bacteria tested using the method.

The substances used in the method are desirably orally acceptable substances. As used herein, the expression 'orally acceptable substance' refers to compounds or compositions of matter that are non-toxic or have a toxicity level which is low enough to allow the substance to be administered to the companion animal at regular intervals and in a dosage that will produce an effect on malodour, either from the animal's mouth or faecal matter. The selection of such substances may be made at a preliminary stage in the screening process, for example by selecting only those substances which are known to have acceptable toxicity levels, or by carrying out toxicity testing of compounds either before or after screening. Suitably, substances identified using the method may subsequently be subjected to toxicity testing to further select for the usefulness in a product for the treatment of malodour.

The screening method provided can comprises, consist essentially of, or consist of any or the particular steps described above, or any combination of these steps, in any number or any order.

DETAILED DESCRIPTION

The present method will now be particularly described by way of example. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. The examples refer to the accompanying diagrammatic drawings in which:

Figure 9:
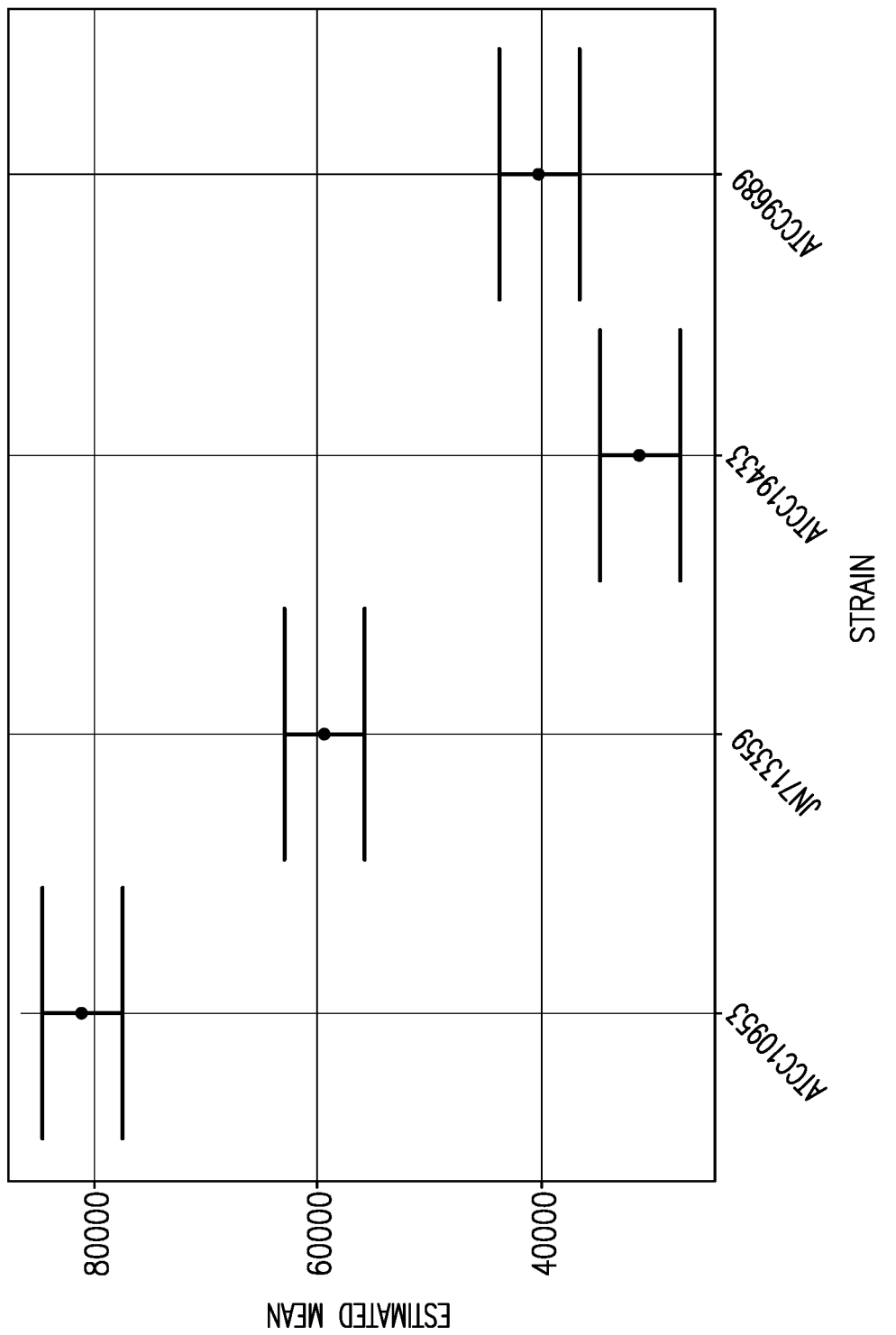

FIG. 9. Level of VSCs generated by canine oral and faecal strains. ATCC10953: *Fusobacterium nucleatum*: known bad breath causing bacteria in human, also isolated from canine oral cavity. JN713359: *Porphyromonas macacae*: a periodontal disease associated bacteria in canine oral cavity. ATCC19433(006): *Enterococcus faecalis*: canine faecal bacteria also found in human faeces, ATCC9689 (7276): *Clostridium difficile* another bacteria isolated from canine faeces, that has been isolated from elsewhere previously.

Figure 10:
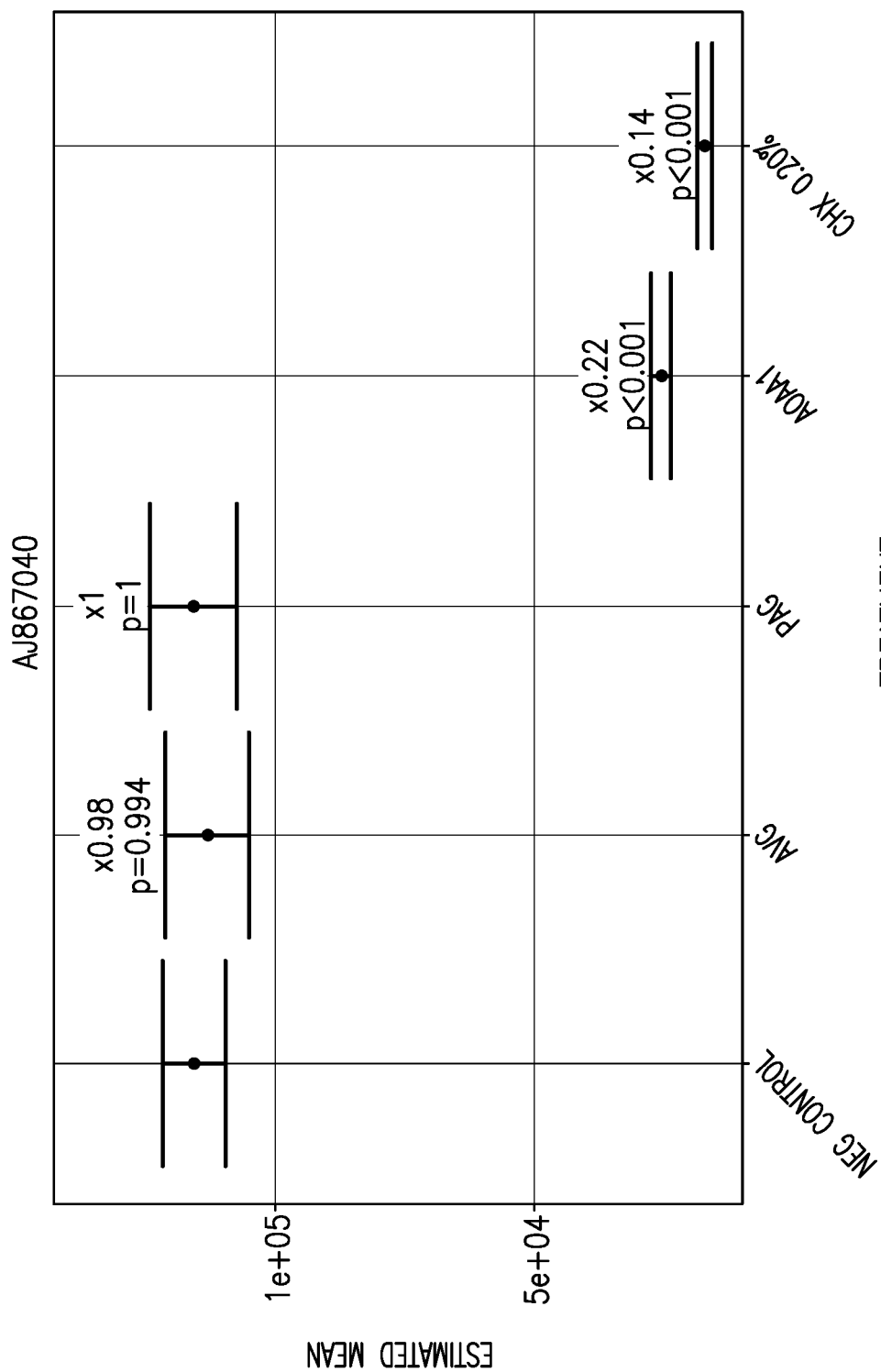

FIG. 10 shows the results of an experiment to determine estimated mean VSC produced by bacteria *Fusobacterium* sp RMA1065 (AJ867040) with and without active substances. Annotations show fold changes versus the control and p-values of significance.

Figure 11:
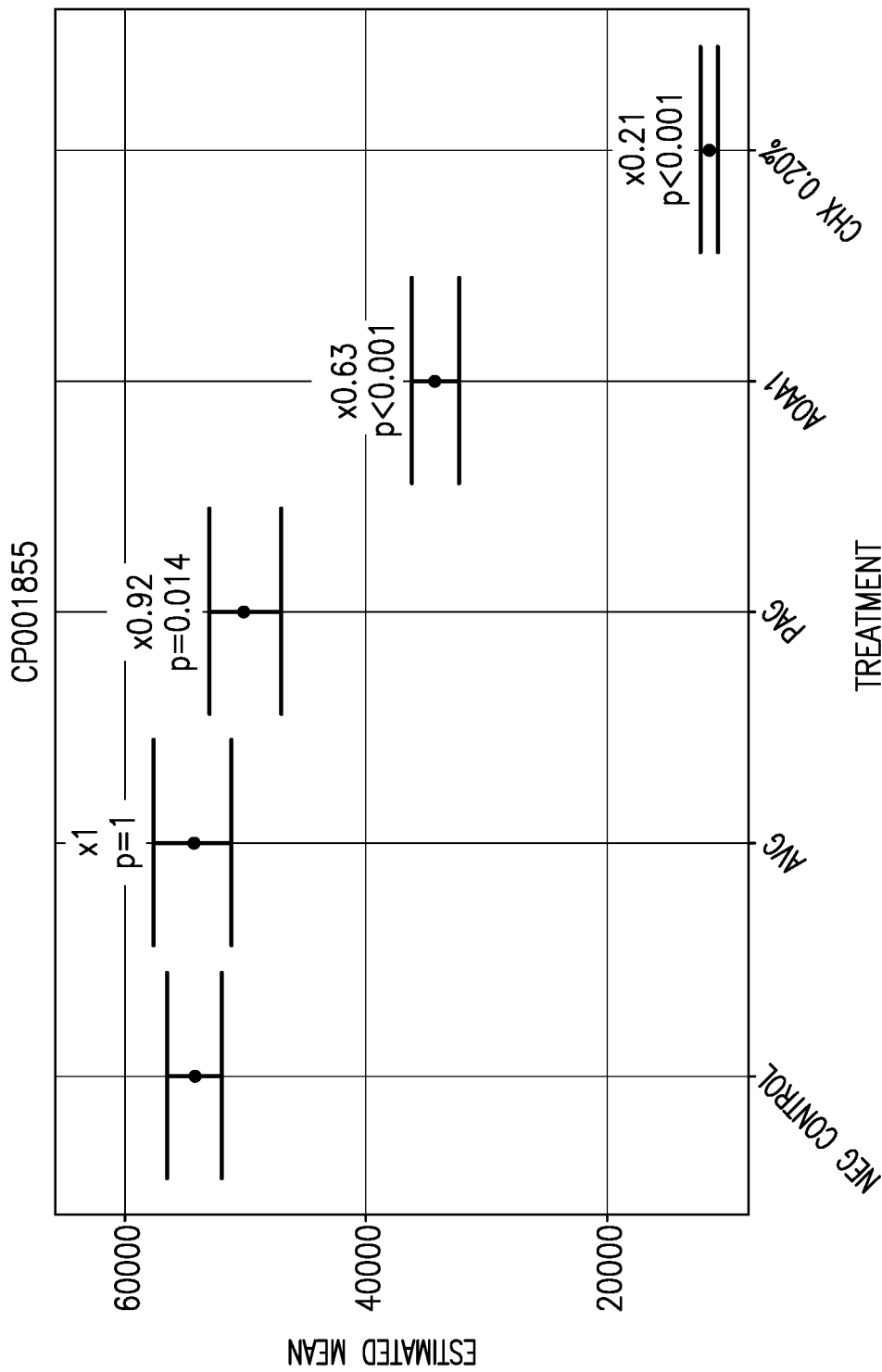

FIG. 11 shows the results of an experiment to determine estimated mean VSC produced by *E. coli* bacteria (CP001855) with and without active substances. Annotations show fold changes versus the control and p-values of significance.

Figure 12:
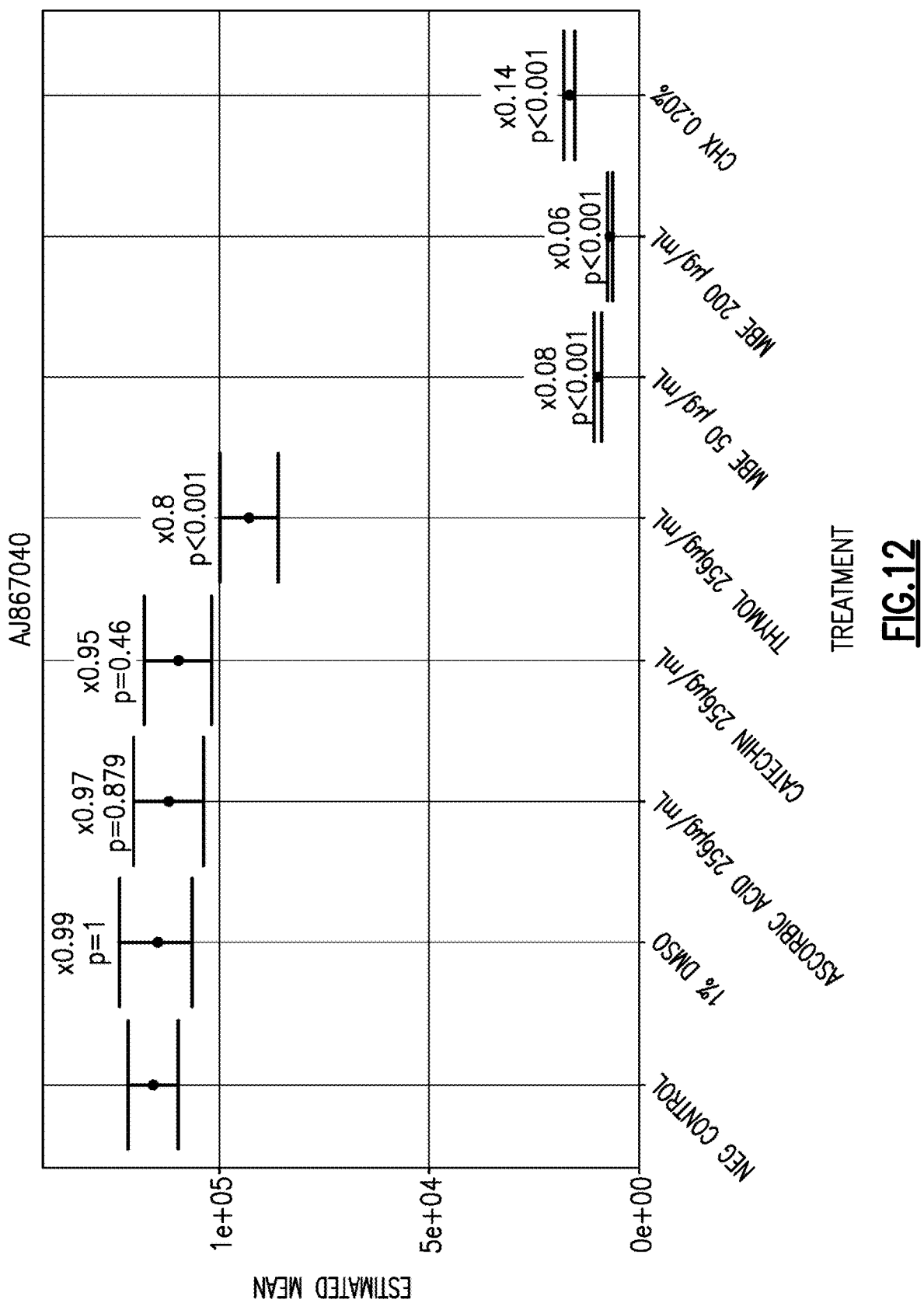

FIG. 12 shows the results of an experiment to determine the estimated mean VSC produced by *Fusobacterium* sp RMA1065 (AJ867040) with and without test substances in accordance with the screening method. Annotations show fold changes versus the control and p-values of significance.

Figure 13:
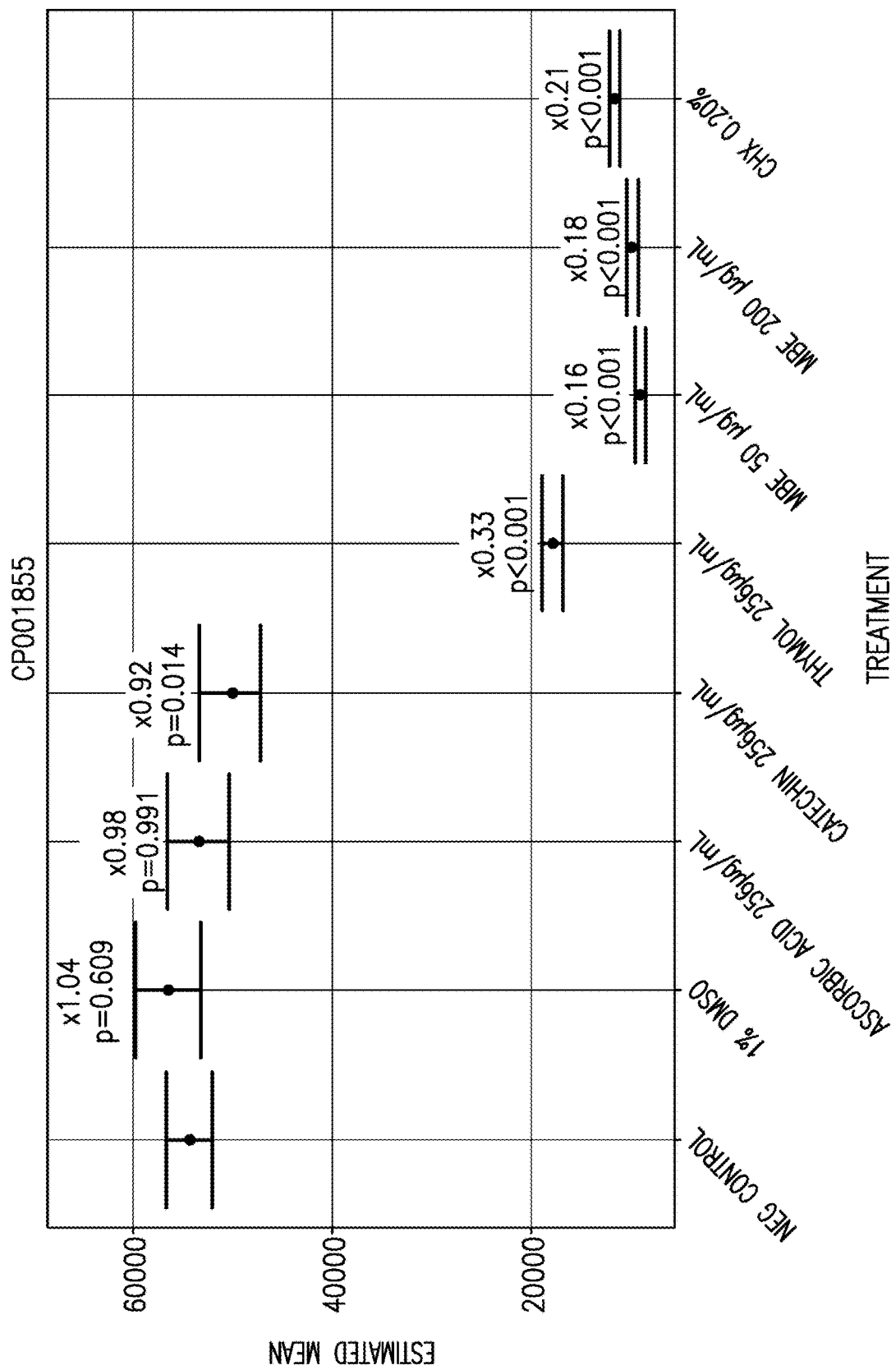

FIG. 13 shows the results of an experiment to determine the estimated mean VSC produced by *E. coli* bacteria (CP001855) with and without test substances in accordance with the screening method. Annotations show fold changes versus the control and p-values of significance.

EXAMPLE 1

Fluorescent Method for Detecting Hydrogen Sulphide Production and Identification of High VSC Emitting Strains from Oral Cavities of Dogs A range of bacterial samples obtained from isolates from the canine oral cavity as well as two type strains (*F. nucleatum* ATCC10953 and *Escherichia coli* DH5α) were used in the experiment and these are listed in Table 1 hereinafter. All bacteria strains were stored at −80 C°.

TABLE 1

| Genbank Accession Number | Taxonomy |
|---|---|
| JN713478 | Bacteroides heparinolyticus |
| JN713352, JN713353 | Bergeyella_zoohelcum_COT-186 |
| JN713168, JN713169, JN713170, JN713171 | Campylobacter_sp. COT-011 |
| JN713418 | Capnocytophaga_sp._COT-254 |
| JN713473 | Chloroflexi_[G-1]_sp._COT-306 |
| DH5 | Escherichia_coli |
| ATCC10953 | Fusobacterium_nucleatum_ATCC10953 |
| JN713356 | Fusobacteriusp._COT-189 |
| JN713237 | Lachnospiraceae_bacterium_COT-073 |
| JN713178 | Moraxella_sp._COT-017 |
| JN713497 | Moraxella_sp._COT-328 |
| JN713177 | Neisseria_animaloris_COT-016 |
| JN713254 | Neisseria_sp._COT-090 |
| JN713518 | Neisseria_zoodegmatis_COT-349 |
| JN713256 | Pasteurella_dagmatis_COT-092 |
| JN713216 | Peptostreptococcaceae_bacterium_COT-047 |
| JN713315 | Peptostreptococcus_hiranonis_COT-148 |
| JN713198 | Peptostreptococcus_sp._COT-033 |
| JN713350 | Porphyromonadaceae_bacterium_COT-184 |
| JN713276, JN713277 | Porphyromonas_cangingivalis_COT-109 |
| JN713184 | Porphyromonas_gingivicanis_COT-022 |
| JN713220, JN713221 | Porphyromonas_gulae_COT-052 |
| NZ_JRFB00000000 | Porphyromonas_macacae COT-192 OH2631 |
| JN713359 | Porphyromonas_macacae_COT-192 |
| JN713457 | Porphyromonas_sp._COT-290 |
| JN713343 | Synergistales_bacterium_COT-178 |

COT: Canine Oral Taxon, an identification system used at HOMINGS systems for microbial taxonomy. All strains used were isolated from canine oral cavities. Strain identification was made within 98% identity to the Genbank identifications and type strain mentioned above.

The C-S lyase activity was measured in order to quantitate VSC production by the bacteria. This was conducted by using monobromobiname, a fluorescent probe for thiol. The bacteria were washed and resuspended in Tris buffer (pH 8.5) at OD=1.0. The 250 μL reaction mix contained 4 mM benzylcysteine, 100 μM monobromobimane, 10 μM pyridoxal 5'-phosphate, 50 μL of the bacteria suspension and was made up to 250 μL with tris buffer (pH 8.5). The mix was incubated anaerobically for 45 minutes at 37 C°. The C-S lyase activities were determined based on fluorescence at 490 nm (em) upon excitation at 385 nm (ex).

All measurements were performed in biological duplicate with each repeated in technical triplicates, creating total of 6 data points per strain. Blank measurements (containing buffer instead of crude extract) were used to correct the values derived from the substrate. The standard curve was measured using Benzyl mercaptan at 8-128 μM. The protein concentration of the bacteria suspension was determined by means of a commercially available BCA kit in accordance with the manufacturer's method. The specific C-S lyase activity was calculated by dividing the increase in fluorescence equivalent to Benzyl mercaptan concentration by the total protein content of the suspension in mg and expressed as unit which was defined as "nM Benzyl mercaptan release/ μg protein/minute".

Figure 1:
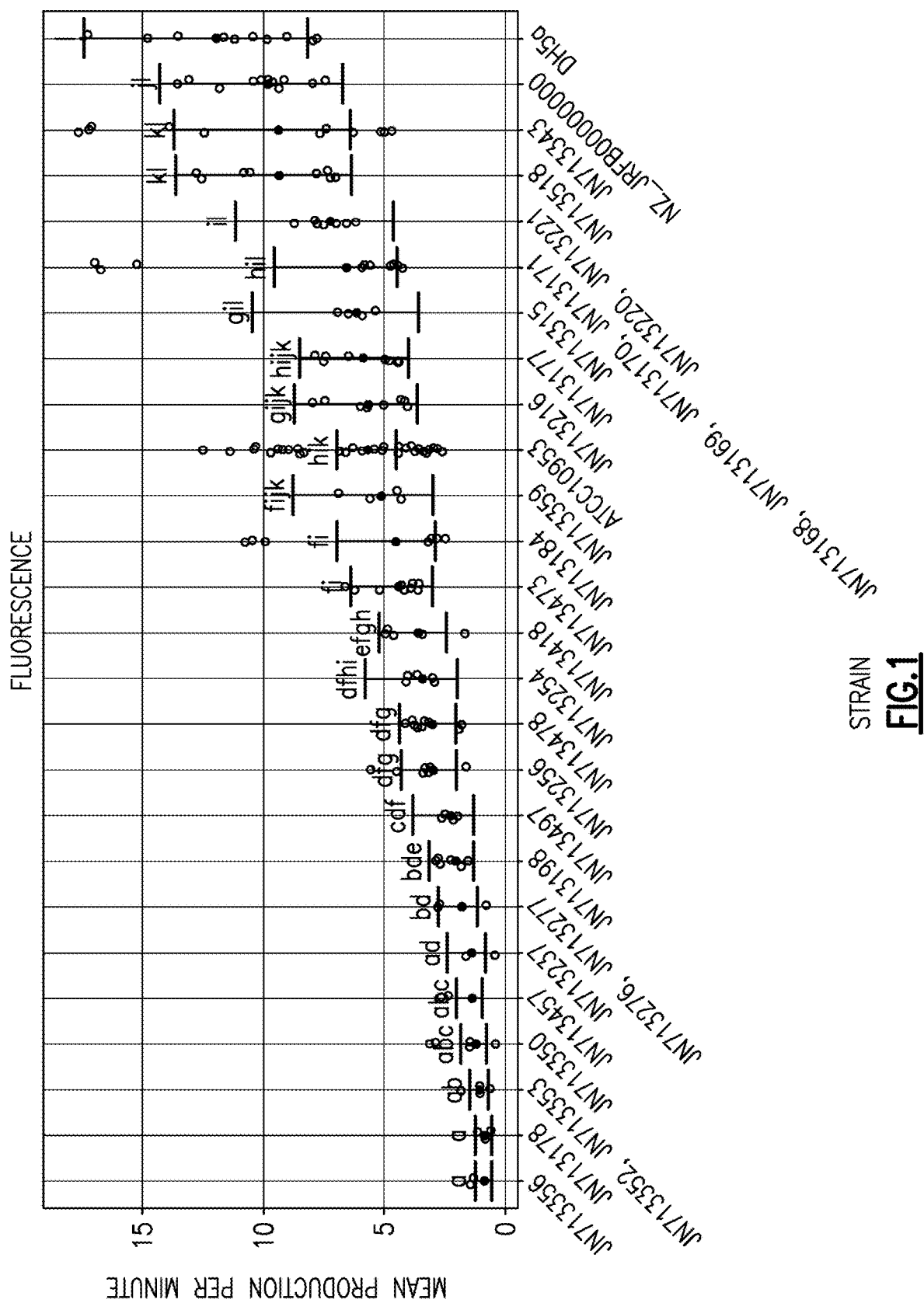
FIG. 1 shows the results of an experiment to determine estimated mean VSC production per minute indicated by the fluorescence measures (mBB method). Annotated letters indicated Tukey groups from the pairwise comparisons where bacterial strains sharing no letters were significantly different (for example DH5α versus *Neisseria animaloris* JN713177).

The results are shown in FIG. 1.

An additional experiment was carried out using a different hydrogen sulfide method. In this case, bacteria cultured in Brian Heart Infusion media (BHI) were pelleted at 2000×g for 10 minutes then transferred to fresh BHI at pH 8.5 at OD600=0.5. Three mL of BHI suspension was added to a 7 mL bijoux vial.

Fresh BHI was used as the negative control. All samples were conditioned in an anaerobic cabinet at 38 C° for at least half an hour prior to the following steps. A 50 μL of 0.05% (w/w) cysteine solution was then added to the samples. In this case, a lead acetate strip was placed so as to hang from the lid of bijoux vial in order to avoid contact with the solution. Samples were incubated for one hour anaerobically. Lead acetate strips were then removed from the vials and visually measured for their colour intensity in a scale of 0-10 with 10 being the most intense black.

Figure 2:
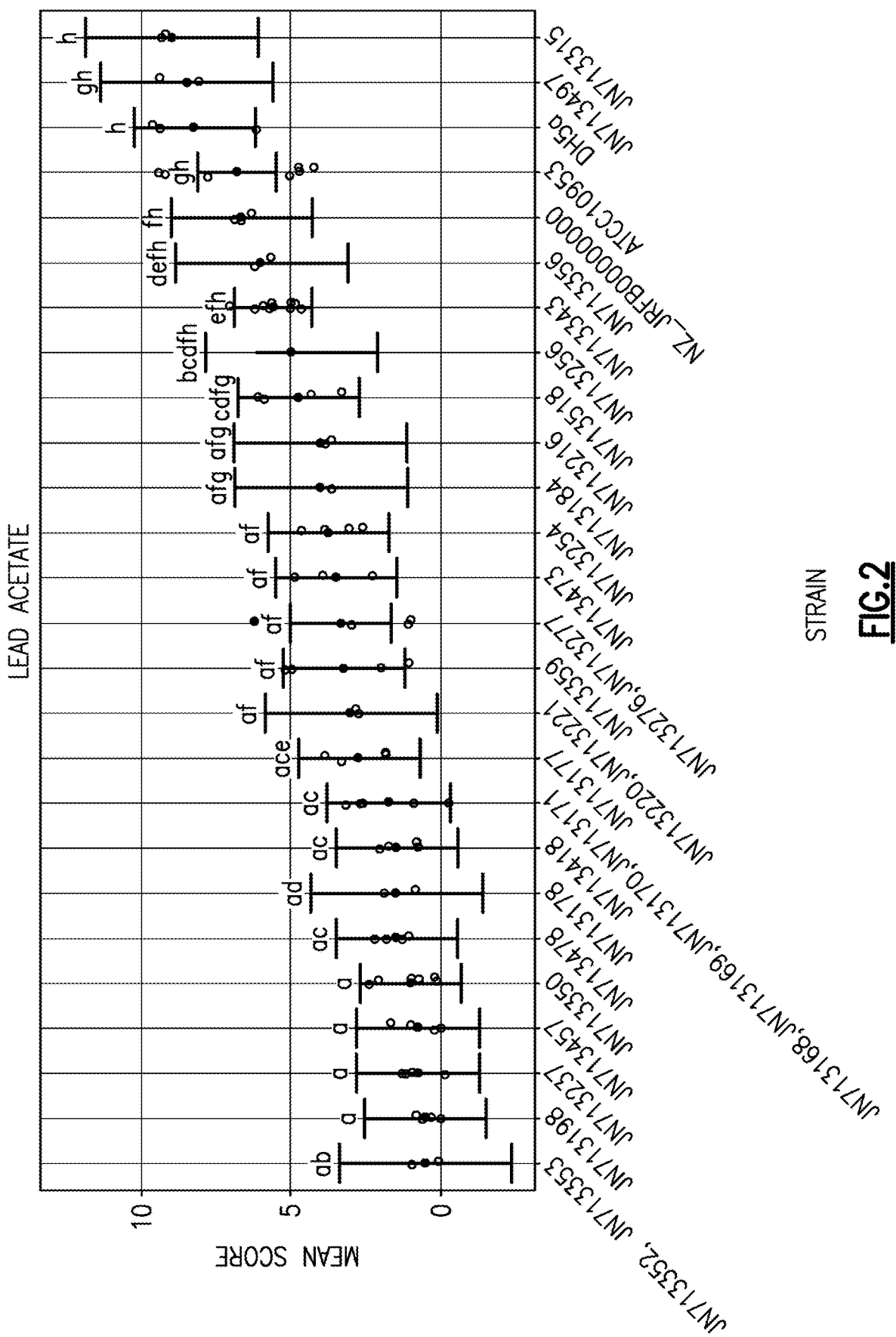
FIG. 2 shows the results of an experiment to determine estimated mean VSC production indicated by the lead acetate measures. Annotated letters indicate Tukey groups from the pairwise comparisons where bacterial strains sharing no letters were significantly different (for example *Peptostreptococcus hiranonis* JN713315 versus *Neisseria zoodegmatis* JN713518).

Results are shown in FIG. 2.

Figure 3:
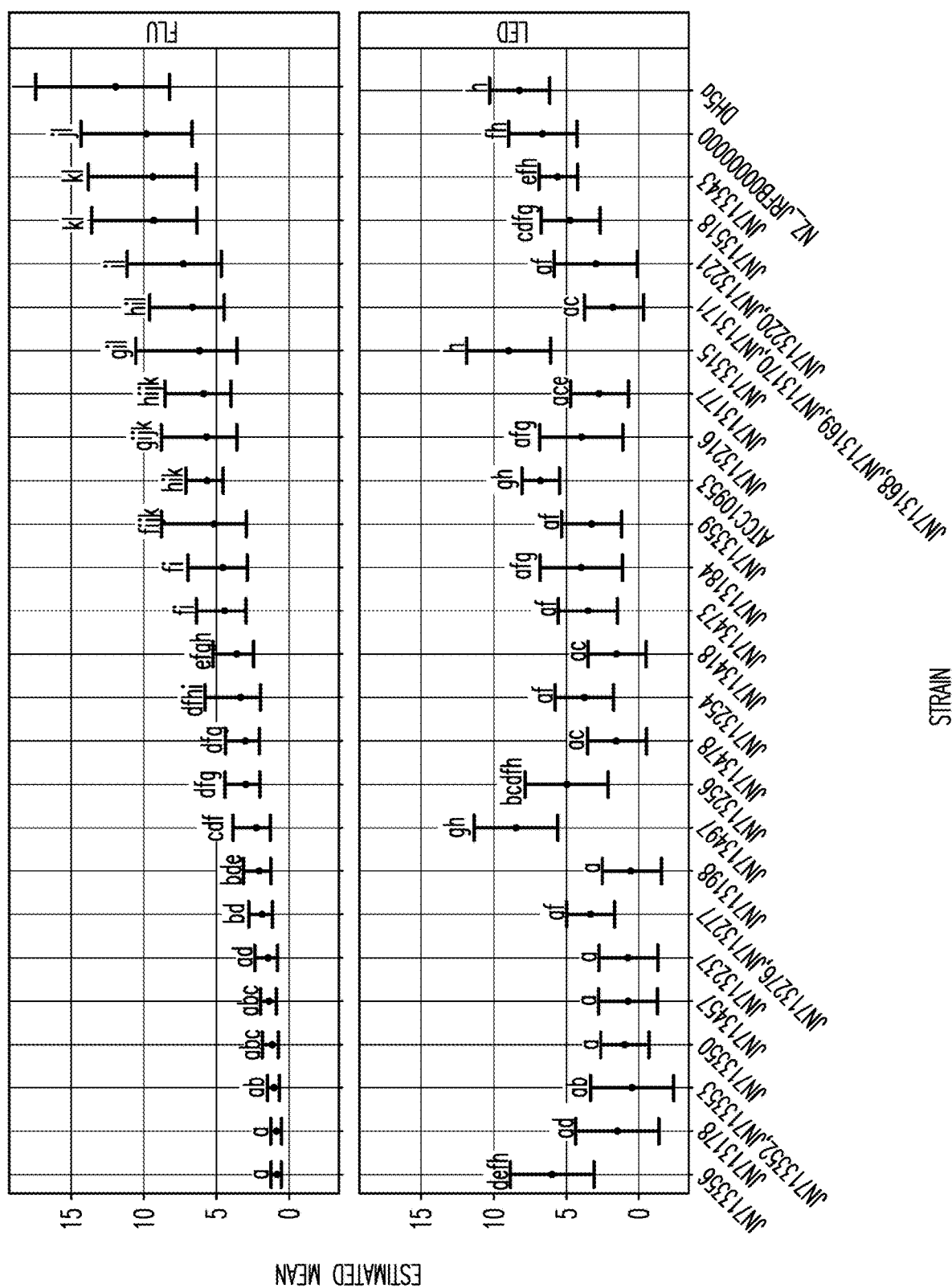
FIG. 3 shows estimated means from the results illustrated in FIGS. 1 and 2, matched by bacterial strain.
Figure 4:
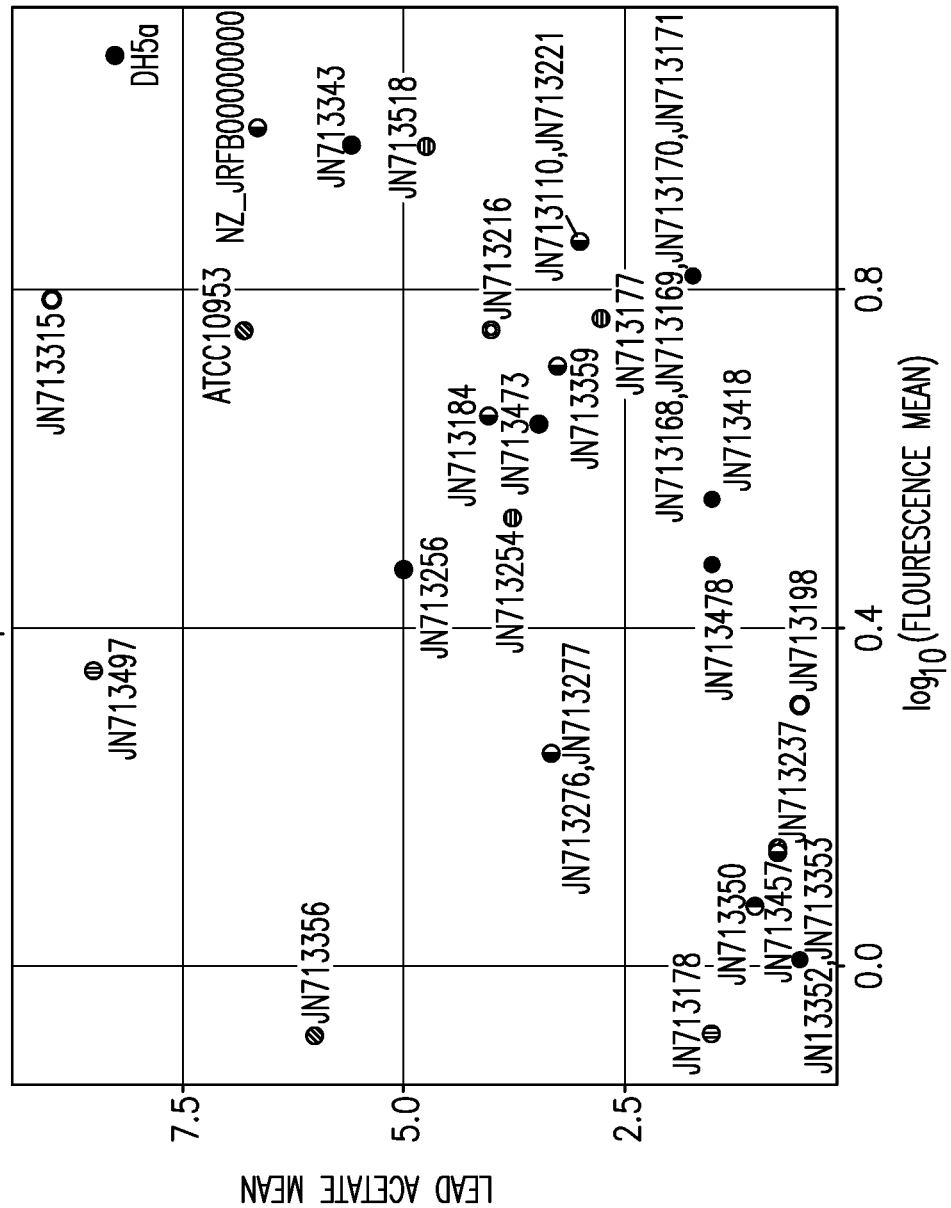
FIG. 4 shows mean lab measures for each bacterial strain tested with the estimated correlation and p-value for a significant difference from 0.

Analysis of the two lab measurements of VSC production indicate clear patterns in the produced quantities from the bacterial strains, FIG. 1 and FIG. 2. For both measurements significant differences were found between certain pairs of bacteria. For example, DH5α versus Neisseria animaloris JN713177 in the fluoroscopy data. Comparing the two lab measures, FIG. 4, indicates significant correlation between the two although with a different order of bacteria when sorted by production, FIG. 3.

As a result, six bacteria, which were either high VSC emitters and/or isolable from various areas of a dog's mouth were selected for further work. These were *Escherichia coli* DH5, *Porphyromonas macacae* (JN713359 and NZ_JRFB00000000), *Synergistales* sp. (JN713343), *Peptostreptococcus hiranonis* (JN713315), *Fusobacterium nucleatum* (OH65) and *Neisseria zoodegmatis* (JN713518). Three of these *Escherichia coli* DH5, *Porphyromonas macacae* (JN713359 and NZ_JRFB00000000) and *Synergistales* sp. (JN713343) were particularly useful as they were the highest emitters with a similar level of statistical significance.

EXAMPLE 2

Proof of Principle for Screening Method Using mBB with Known Actives

Two test strains, *Fusobacterium nucleatum* (ATCC10953) and *Porphyromonas macacae* (JN713359), were selected for a proof of concept experiment. Known active ingredients in amounts summarised in Table 2 below, were tested using mBB method described above in Example 1. Each active ingredient was added to the bacteria resuspension immediately before its addition in the well. The following active ingredients were tested for this proof of concept experiment.

TABLE 2

| Active | Final concentration used | Reported concentration |
|---|---|---|
| Chlorohexidine (CHX) | 0.12% w/w | 0.12% w/w |
| DL-Propargylglycine (PAG) | 100 μM | 40 μM |
| O-Carboxylmethyl-hydroxylamine hemihydrochloride(AOAA) | 20 μM | 10 μM |
| Aminoevulinic acid (AVG) | 5 μM | 1 μM |

Figure 5:
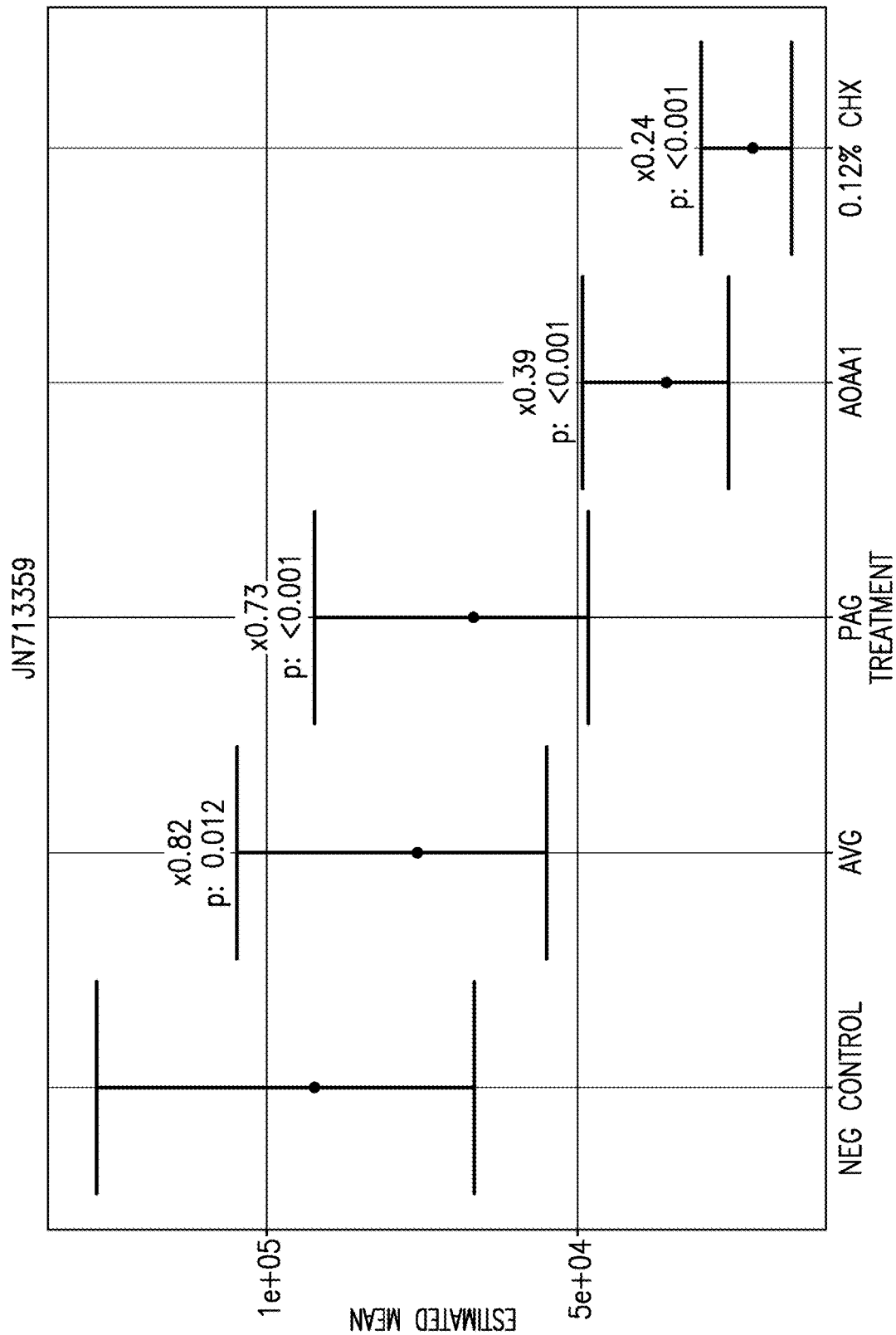
FIG. 5 shows the results of an experiment to determine the estimated mean VSC produced by bacteria *Porphyromonas macacae* JN713359 with and without known active substances. Annotations show fold changes versus the control and p-values of significance.
Figure 6:
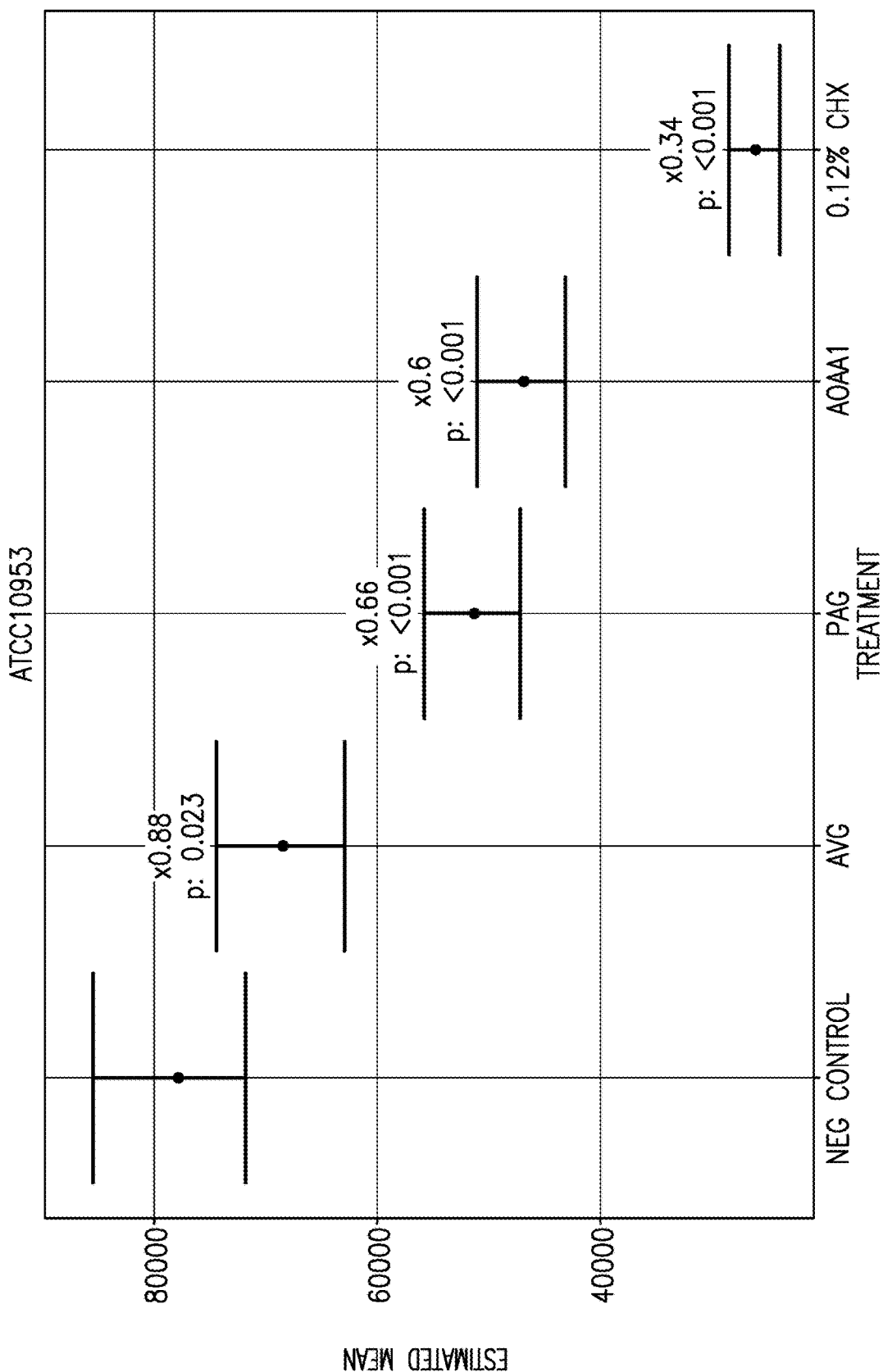
FIG. 6 shows the results of an experiment to determine estimated mean VSC produced by bacteria *Fusobacterium nucleatum* ATCC10953 with and without active substances. Annotations show fold changes versus the control and p-values of significance.

The selection of actives was based on the cost and volatility. The results are shown in FIGS. 5 and 6 respectively. These results show that the each of the active ingredients tested reduced the VSC production, confirming that this method provides an indicator of activity.

The results from validation using known actives also showed that the method will identify agents that target the underlying causes of oral malodour and steers away from masking agents. Chlorohexidine (CHX) is a widely prescribed antiseptic in the form of an oral rinse after oral surgery whereas the other three tested actives are known inhibitors for VSC producing enzymes, i.e. cystathionine β synthase (CBS) and cystathionine γ lyase (CSE). Only CHX has been reported to have activity as an antiseptic or disinfectant. This demonstrates that the method is capable of identifying and evaluating enzyme inhibitors as well as antimicrobials.

Another noteworthy point is that the mBB method in particular leverages the enzyme degradation of amino acid to VSC, therefore it will be able to screen out masking agents.

EXAMPLE 3

Use of Screening Method to Test a Range of Substances as VSC Inhibitors

The method of Example 2 was then repeated using a range of substances of unknown activity. These are listed in the following Table 3.

TABLE 3

| Active | Comments |
| --- | --- |
| Vitamin C (ascorbic acid) | The optimal pH for the target enzyme is in the alkaline range. The impact on addition of food grade acid and lowering pH may impact on enzyme activity |
| Tea polyphenol (catechin) | Green tea extract is included in many products active in breath freshening. Polyphenols and catechins have previously been reported as having anti-VSC- activity |
| Thymol | An active anti-microbial in commercial mouthwash and thus often used as the positive control for personal care/food grade oral care products where comparison with prescription antiseptic such as chlorhexidine may not be relevant. |
| Magnolia Bark Extract (MBE) | known food grade anti-microbial natural product (see for example U.S Pat. No. 8,012,514) |
| Chlorhexidine | The gold standard antiseptic for oral microbiology |

Of the above, Chlorhexidine (CHX) acted as a positive control, and buffer (Neg control) and 1% DMSO as negative controls. 1% DMSO was also used to dissolve the actives.

MBE at both concentrations showed inhibitory activities with p<0.01.

Figure 7:
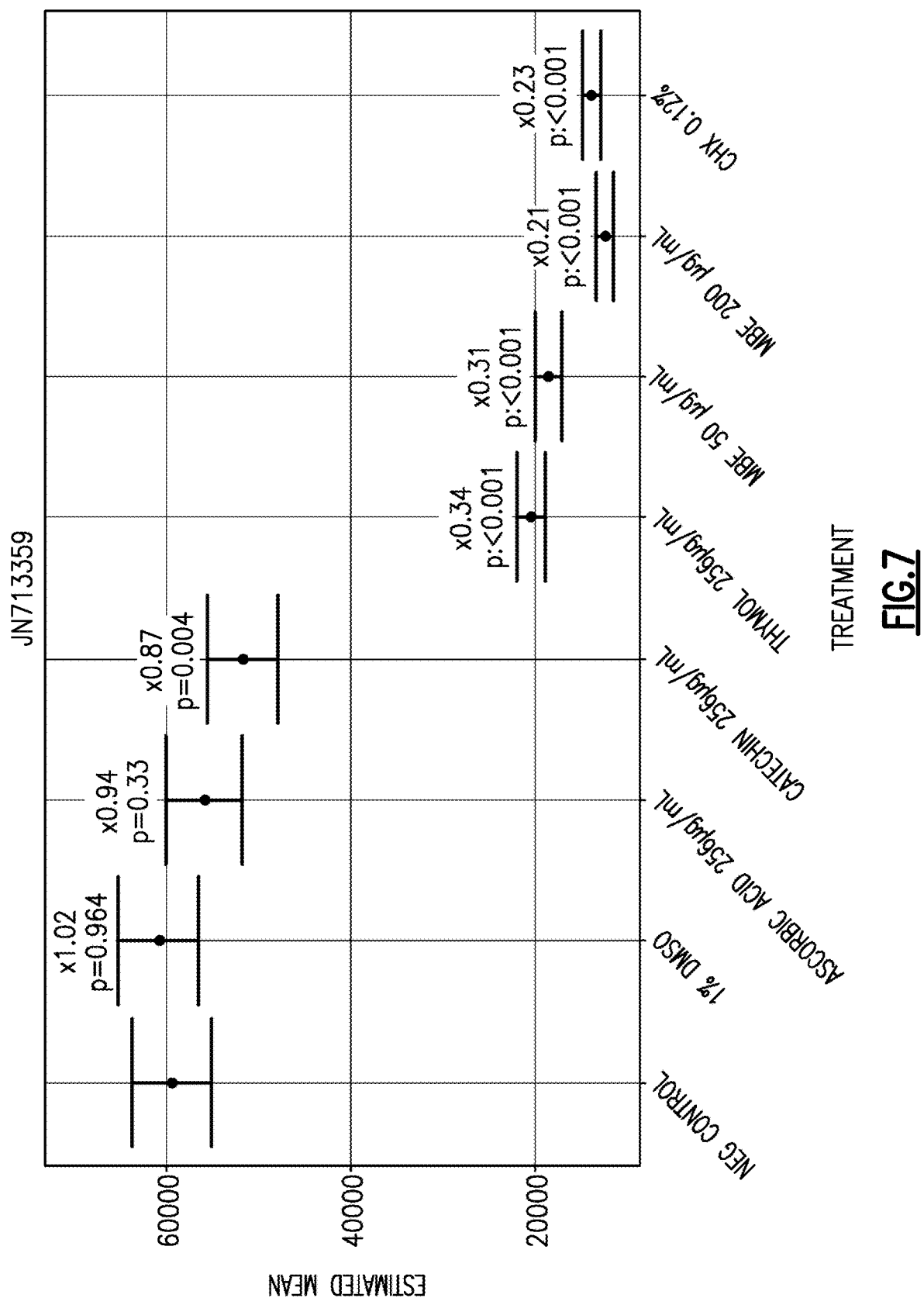
FIG. 7 shows the results of an experiment to determine the estimated mean VSC produced by bacteria *Porphyromonas macacae* JN713359 with and without test substances in accordance with the screening method. Annotations show fold changes versus the control and p-values of significance.
Figure 8:
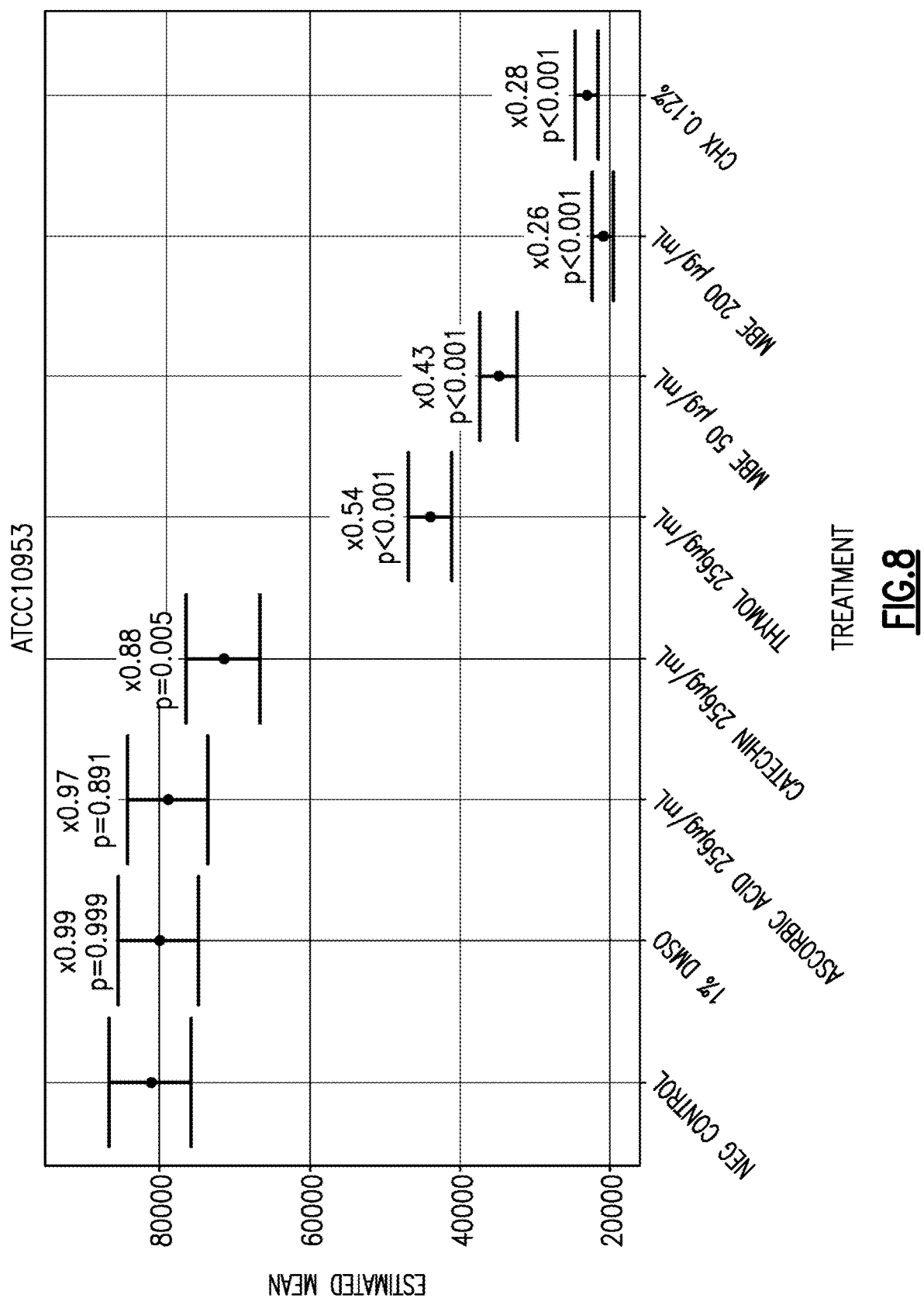
FIG. 8 shows the results of an experiment to determine the estimated mean VSC produced by bacteria *Fusobacterium nucleatum* ATCC10953 with and without test substances in accordance with the screening method Annotations show fold changes versus the control and p-values of significance.

The results are shown in FIGS. 7 and 8. The analysis of the bacterial VSC production, under several active ingredients, indicated significant reductions in production for all ingredients aside from DMSO, ascorbic acid and catechin. For example with strain *Porphyromonas macacae* JN713359 the 0.12% CHX treatment resulted in only 25% the quantity of VSC produced as the control.

FIG. 7 shows the results from canine oral bacteria and FIG. 8 with human oral bacteria often used as the gold standard for bad breath causing bacteria (*Fusobacterium nucleatum*). FIG. 8 confirms that the method of the invention works with human oral species and thus validates results from canine oral bacteria.

EXAMPLE 4

Demonstration of Similar VSC Production from Faecal Bacteria

The method of Example 2 was repeated using two canine faecal bacteria, alongside two canine oral bacteria. The results are shown in FIG. 9. These results show that VSCs are produced, albeit in lower levels, by faecal bacteria and that therefore the method of the invention may be used to screen substances that could impact on faecal malodour also.

In such cases, any substances tested would either be required to administered orally, and so be resistant to degradation in the stomach, and/or be formulated with for example an enteric coating, to protect the substance as it passes through the gut of the companion animal.

In addition, the method of example 2 was repeated using two strains of fecal bacteria isolated from canine faeces.

In particular, canine faeces were suspended in nutrient broth to form a faecal slurry. Dilutions of the slurry were inoculated on varied type of agar plates and incubated in anaerobic conditions. Individual bacterial colonies were selected and re-streaked on the same type of agar for isolation, and propagated. Isolated bacterial species were then stored by suspending in BHI/glycerol solution and frozen at −80° C. Strains were then raised by taking a loop of inoculum from the frozen vial, steaking on Columbia blood agar and incubating in anaerobic conditions for a minimum of 24 hours. Species are then identified by 16S sequencing for selection.

Two faecal isolates that generated VSC were identified as *fusobacterium* sp. RMA 1065 (genbank accession number AJ867040) and as an *E. coli* strain (genbank accession number CP001855. The results obtained when these bacteria were subjected to the method of Example 2 are shown in FIGS. 10 and 11 respectively. Again, these results show that the each of the active ingredients tested reduced the VSC production, confirming that this method provides an indicator of activity.

The same two strains were then tested using the method of Example 3. Results are shown in FIGS. 12 and 13. The analysis of the bacterial VSC production, under several active ingredients, indicated significant reductions in production for all ingredients aside from DMSO, ascorbic acid and catechin as before. Thus, the faecal bacteria appear to respond in a similar fashion to the oral bacteria tested.

What is claimed is:

1. A method for screening substances for their ability to reduce malodours from emanations from an animal, said method comprising determining the effect of said substances on the C-S lyase activity of bacteria present in an oral cavity of an animal that emit volatile sulphuric compounds (VSCs), by contacting a test substance with a sample comprising said bacteria or a supernatant obtainable from a culture of said bacteria in the presence of a substrate for a C-S lyase, detecting the levels of thiol production from said sample, and comparing the results with those obtained from said sample in the absence of said substance, wherein the method does not include lysis and wherein the bacteria are selected from selected from the group consisting of *Escherichia coli* DH5, *Porphyromonas macacae* (Genbank Accession No. JN713359), *Porphyromonas macacae* (Genbank Accession No. NZ_JRFB00000000) and *Synergistales* sp. (Genbank Accession No. JN713343).

2. A method according to claim 1 wherein the sample comprises live bacteria.

3. A method according to claim 1 wherein the C-S lyase is cystathione-β-lyase and the substrate is benzylcysteine.

4. A method according to claim 1 wherein levels of thiol production are detected using a fluorometric method.

5. A method according to claim 4 wherein levels of C-S lyase activity are determined by culturing live bacteria in the presence of both a substrate for the enzyme, and an indicator which reacts with a thiol to produce a fluorescent signal.

6. A method according to claim 5 wherein the indicator is a bimane dye derivative.

7. A method according to claim 6 wherein the bimane dye derivative is monobromobimane (3-(bromomethyl)-2,5,6-trimethyl-1H,7H-pyrazolo[1,2-α]pyrazole-1,7-dione).

8. A method according to claim 1 wherein a co-enzyme is added to the sample to catalyse the enzymatic reaction.

9. A method according to claim 8 wherein the co-enzyme is pyridoxal-5'-phosphate.

10. A method according to claim 1 wherein the animal is a companion animal.

11. A method according to claim 1 wherein the bacteria used is one which emits high levels of VSCs.

12. A method according to claim 11 wherein the bacteria is *Escherichia coli* DH5α.

13. A method according to claim 1 wherein the bacteria used has been identified as being present in plaque biofilms, saliva, or from the buccal region or dorsum part of the tongue, of one or more companion animals.

14. A method according to claim 13 wherein the bacteria used is identified as being one that emits a higher level of VSCs as compared to levels of VSCs of other bacteria identified as being present in the oral cavity.

15. A method according to claim 13 wherein the companion animal is a dog.

16. A method for screening substances for their ability to reduce malodours from emanations from an animal, said method comprising determining the effect of said substances on the C-S lyase activity of bacteria that emit volatile sulphuric compounds (VSCs), by contacting a test substance with a sample comprising said bacteria or a supernatant obtainable from a culture of said bacteria in the presence of a substrate for a C-S lyase, detecting the levels of thiol production from said sample, and comparing the results with those obtained from said sample in the absence of said substance, wherein said method is carried out using more than one bacterial strain selected from the group consisting of *Escherichia coli* DH5, *Porphyromonas macacae* (Genbank Accession No. JN713359), *Porphyromonas macacae* (Genbank Accession No. NZ_JRFB00000000) and *Synergistales* sp. (Genbank Accession No. JN713343), and does not include homogenisation and lysis.

17. A method according to claim 16 which further comprises selecting target substances for the treatment of malodour which inhibit VSC production from more than one of the bacterial strains tested.

18. A method according to claim 16 wherein the method is carried out in a combined culture.

* * * * *